United States Patent [19]

Telfer et al.

[11] 4,358,682

[45] Nov. 9, 1982

[54] NEUTRON INTERFACE DETECTOR

[75] Inventors: Alexander Telfer, Houston; Dale H. McMillan, Katy, both of Tex.

[73] Assignee: Shell Oil Company, Houston, Tex.

[21] Appl. No.: 165,993

[22] Filed: Jul. 7, 1980

[51] Int. Cl.³ .................... G01N 23/00; G01T 3/00
[52] U.S. Cl. .................... 250/357.1; 250/390; 378/52
[58] Field of Search .............. 250/357, 390, 391, 392

[56] References Cited

U.S. PATENT DOCUMENTS

| 2,972,050 | 2/1961 | Allen | 250/357 |
| 3,389,250 | 6/1968 | Clemens | 250/357 |
| 3,716,711 | 2/1973 | Olesen | 250/43.5 |
| 4,038,548 | 7/1977 | Charlton | 250/390 |
| 4,216,376 | 8/1980 | Griffin et al. | 250/357 |

Primary Examiner—Alfred E. Smith
Assistant Examiner—Janice A. Howell

[57] ABSTRACT

A fixed neutron backscatter level detector for hydrogen containing liquids or solids. The detector comprises a source of fast neutrons and a thermal neutron detector disposed to measure thermal neutrons that are backscattered by the liquids or solids.

6 Claims, 4 Drawing Figures

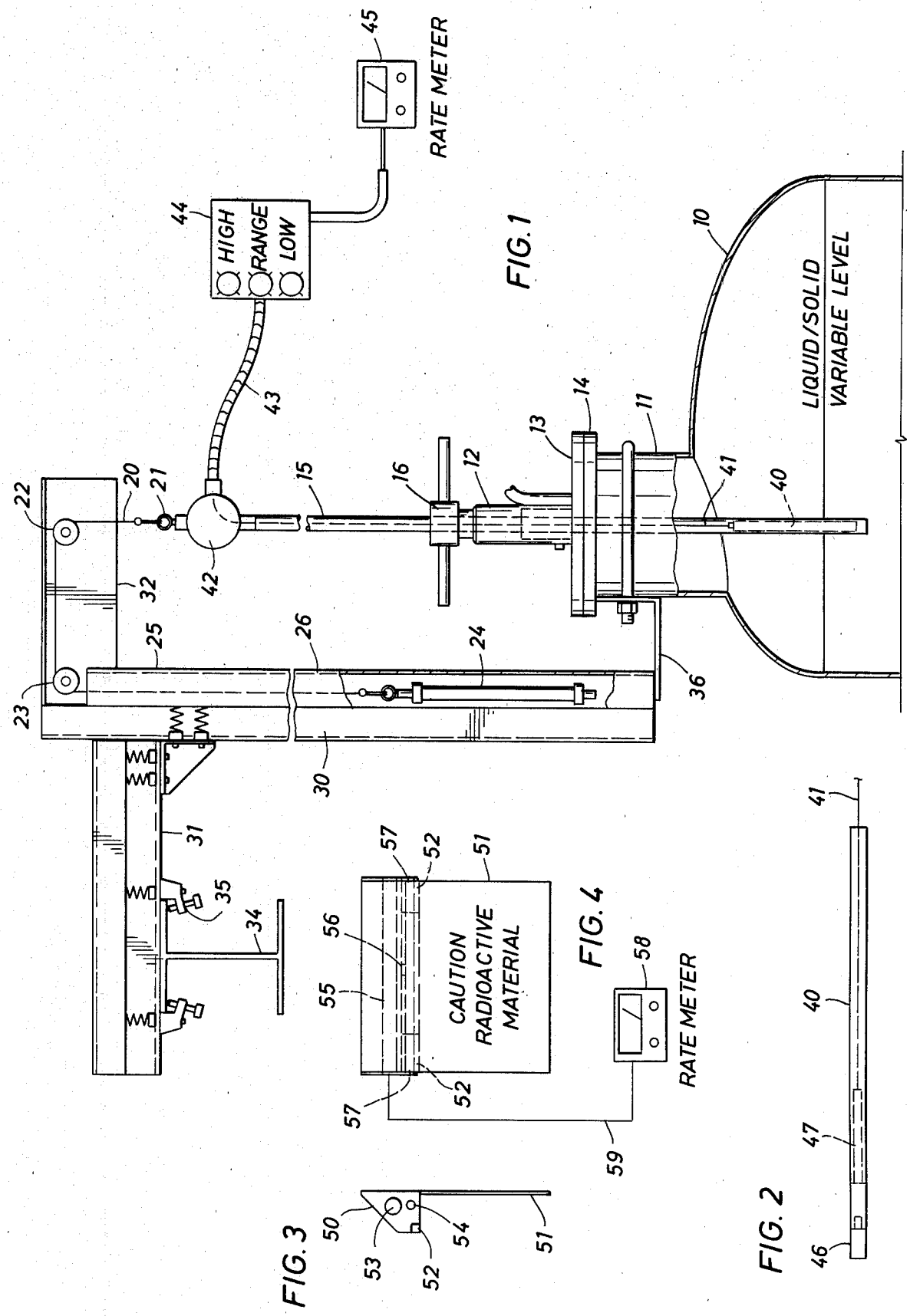

NEUTRON INTERFACE DETECTOR

RELATED PATENT APPLICATIONS

The present invention is related to an invention described in a co-pending application entitled "Neutron Interface Detector" by Griffin et al., filed June 22, 1978, Ser. No. 918,120, now U.S. Pat. No. 4,216,376.

BACKGROUND OF THE INVENTION

The present invention relates to liquids or solids (hereinafter referred to as material) level detectors and particularly to liquids or solids level detectors that utilize the backscattering of neutrons to detect the level of hydrogen containing liquids or solids in a closed vessel. In the above referenced co-pending application there is described and claimed a portable liquid level detector which utilizes a source of fast neutrons and a detector for slow neutrons. As the detector is moved along the wall of a vessel containing a liquid including hydrogen as one of its components, the level of the liquid is detected by the change in the number of slow neutrons being counted. The number of backscattered slow neutrons is directly related to the number of hydrogen atoms present for slowing the fast neutrons from the source. Thus, as the detector moves from the liquid or solid to the gas phase the number of backscattered slow or thermal neutrons produced will decrease. This decrease in the number of slow neutrons is used to indicate the level of the liquid within the closed vessel.

While the detector described in the co-pending application is useful as a portable instrument for making routine surveys of closed vessels such as those used in a refinery, there is a need for stationary material level detectors. While this need has been filled in the past by float-type level detectors, these are not entirely satisfactory in all processes in a refinery and chemical plants. This is especially true where the material has a relatively high viscosity where the float does not readily respond to the material level. Also, the use of floats requires mechanical connections to the interior of closed vessels that must be installed when the equipment is originally built. The presence of mechanical connections also results in maintenance problems since it is difficult to have access to the location of the float without shutting down the process.

In the past, attempts have been made to use gamma type sources and suitable detectors for detecting levels. The use of gamma sources requires that the source be placed on on side of the vessel while the detector is placed on the other side. Thus, again it is necessary to design the particular vessel with suitable mounting means for the source and detector. Unless relatively large gamma sources are used, it is impossible for the gamma rays to penetrate the thick steel walls of most vessels and thus it is necessary to mount the source inside the vessel so that the gamma rays can travel across the material contained in the vessel. Further, in the case of vessels having baffles or stirring mechanisms or other equipment mounted inside the vessel, it is difficult to install a gamma source so that it will have a straight line or path to the detector. If the gamma ray strikes the stirrer or baffles within the vessel, it is deflected and will not impinge upon the detector.

BRIEF DESCRIPTION OF THE INVENTION

The present invention utilizes the liquid level detector described in the co-pending application to provide a fixed level detector for monitoring or controlling the material level within a closed vessel. In particular, the detector is used to monitor a material level in a closed vessel containing hydrogen bearing material such as vessels found in refinery and chemical plants. In one embodiment of the invention the detector of the co-pending application is lowered through a pipe well located in the top of a vessel to the desired material level in the vessel. The supporting cable means for the detector is so designed that the detector position within the vessel can be raised or lowered to change the material level in the vessel. In the alternative, the detector can be raised and lowered within the vessel to determine the material level within the vessel. The signal from the detector is provided to a rate meter which can be calibrated to provide a direct readout of the material level.

In addition, the detector is completely enclosed in an elongated tube so that as it is raised and lowered within the pipe well it is isolated from the material within the vessel. Thus, by designing the tubular enclosure to withstand the pressures in the vessel and providing a suitable seal around the cable where it exits from the top of the pipe well, the detector can operate within the atmosphere present in the vessel.

Another embodiment of the invention comprises a simple housing containing the source and detector which can be attached to the external wall of a vessel at the desired location of the material level within the vessel. The housing can be attached either by suitable fastening means which are welded to the vessel wall or by the use of magnetic means. Since the level of radioactivity is very low, no shielding of the housing is required. The signal from the detector can be led to a remote location where the level within the vessel can be monitored.

BRIEF DESCRIPTION OF THE DRAWINGS

The present invention will be more easily understood from the following detailed description of the preferred embodiments when taken in conjunction with the attached drawings in which:

FIG. 1 is an elevation view partially in section of one embodiment of the invention.

FIG. 2 is an elevation view of the detector used in the embodiment of FIG. 1.

FIG. 3 is an end view of a second embodiment of the invention.

FIG. 4 is a front view of the second embodiment of the invention.

DESCRIPTION OF A PREFERRED EMBODIMENT

Referring now to FIGS. 1 and 2, there is shown an embodiment of the invention in which a probe member is disposed to be raised and lowered within the closed vessel 10. The vessel 10 may be a storage tank, a reaction vessel or similar type of vessel found in a refinery or chemical plant. In addition, the vessel may contain internal structures such as baffles, trays in a column or stirring mechanisms. In refineries and chemical plants substantially all of the materials contain hydrogen and thus the invention can be used to monitor the level of vessels.

The vessel 10 is provided with a conventional pipe well 11 having a flanged connection 14 at its top. Attached to the flange 14 is a companion flange 13 which is provided with a tubular member 12 having a sealing gland arrangement 16 at its top. Tubular member 12 can be welded or similarly attached to the flange 13 which in turn is bolted to the companion flange 14. The detector housing 15 of the present invention comprises a long tubular member which is sealed at its bottom end. The housing should be formed of a material which will withstand the corrosion of the material within the vessel and any pressures or temperatures produced in the vessel. For example, conventional stainless steel tubing will be satisfactory in most installations.

Housing 15 is raised and lowered within the vessel 10 by means of a flexible cable 20 which passes over fixed sheaves 22 and 23. The free end of the cable can be attached to the top of the housing by suitable means such as an eye-bolt 21. The opposite end of the cable is provided with a counterweight 24 which slides up and down and is confined by tubular member 25. The cable and counterweight arrangement can be supported by suitable structural members 30, 31 and 32 which can be attached to structural members adjacent the vessel such as an I-beam 34 by the use of clamps 35. Similarly, clamp members 36 may be used to support the bottom of the cable supporting structure 30.

The detector assembly 40 is positioned in the bottom of the housing 15 and coupled by cable 41 to the recording instrument. The cable 41 passes through a swivel connection 42 at the top of the housing 15. In addition, the swivel connection can also be sealed where the instrument is operated in an explosive atmosphere. The cable 41 passes through a flexible connection 43 to a range and sensitivity adjusting circuit 44 whose output is coupled to a rate meter 45 which displays a count of the slow neutrons. Of course, the rate meter 45 can be calibrated to a reading which correlates with the level of the liquid in the vessel 10.

Referring to FIG. 2, there is shown an enlarged view of the detector assembly. The detector assembly is similar to that described in the above co-pending application and comprises the outer tubular member which is provided with a source of fast neutrons 46 at one end. This source of fast neutrons is preferably 0.1 micrograms of Californium 252. This size of source will provide about 0.25 milliroentgens per hour at a distance of one meter from the source. This radiation level is approximately a factor of 10 below the established minimum for a 40-hour work week. The slow neutron detector 47 is mounted adjacent the source at the lower end of the tubular housing and is coupled by the cable 41 to the recording instruments as described above. The outer housing of the detector assembly 40 should have a length of approximately one meter so that personnel can attach the fast neutron source 46 to the end without being exposed to excessive radiation. This type of assembly and its inherent safety is described in the above co-pending application.

Referring now to FIGS. 3 and 4, there is shown a second embodiment of the invention with magnetic means for attaching to the outer wall of a vessel. In particular, the embodiment comprises a housing 50 which is preferably formed of stainless steel or similar material and is provided with two longitudinal bores 53 and 54. The housing 50 can be provided with a flat panel member 51 on which the conventional radiation caution message may be displayed. A means for fastening the housing 50 to the outer wall of the vessel should also be provided and may conveniently comprise magnets 52 embedded in recesses formed in the housing. The use of magnets provides a simple means by which the housing may be attached to the vessel without requiring any welding or previous preparation. Of course, it is also possible in a permanent installation to use screw fastenings or similar devices. The radiation or slow neutron detector 55 is disposed in the bore 53 while the source 56 is disposed in the bore 54. Since the source is in the bore 54, the ends can be plugged or sealed by plugs 57. Plugs 57 may be removable threaded plugs which are provided with safety wires and suitable seals so that visual inspection will indicate whether the device has been tampered with. The detector 55 is coupled by the lead 59 to a rate meter 58 which is similar to that described above with relation to FIG. 1.

In the above embodiment, no precautions are taken for reducing the radiation level to below the very low level inherent in the small size of the source. Normally, the device is installed in a remote area and personnel are not subject to exposure. Further, as explained above, the radiation level at a distance of one meter from the source is a factor of 10 below that presently set by the regulations for a 40-hour work week exposure. If it is desired to reduce the exposure level the shape of the housing 50 can be increased so that approximately a meter of distance is between the personnel and the source. Suitable shielding materials may also be placed around the source to isolate personnel from the radiation.

What is claimed is:

1. An apparatus for measuring the level of a hydrogen containing material in a closed vessel, said apparatus comprising: a tubular member having a closed end that is positioned in said vessel; a probe comprising a source of fast neutrons and means for detecting thermal neutrons, said probe being sized so that it can be inserted in said tubular member; a suspension means coupled to said probe to raise and lower said probe in said tubular member; and counting means coupled to said detecting means for counting the number of thermal neutrons detected.

2. An apparatus as recited in claim 1, wherein said suspension means comprises a cable suspended from a fixed sheave, said cable having one end attached to said probe and the other end attached to a counter balance.

3. An apparatus as recited in claim 2, wherein said probe further comprises a tubular housing, said neutron source being disposed adjacent to one end of said housing, said detecting means being positioned in said housing adjacent to said neutron source and the other end of said housing being attached to said cable.

4. An apparatus as recited in claim 3, wherein said housing has a length sufficient to reduce the radiation level at the end of said housing to which said cable is attached to less than 0.5 milliroentgens per hour.

5. An apparatus for measuring the level of a hydrogen containing material in a closed vessel, said apparatus comprisng: a housing having two parallel bores formed therein; means for mounting said housing to the outer wall of said vessel at the desired level of the material in said vessel with said two bores being substantially parallel to the surface of the material in said vessel; a source of fast neutrons positioned in one of said bores; means for detecting slow neutrons, said detecting means being positioned in the other bore of said housing; and counting means coupled to said detecting means for counting the number of slow neutrons detected.

6. An apparatus as recited in claim 5, wherein said mounting means is magnetic.

* * * * *